US008906327B2

(12) United States Patent
Williams et al.

(10) Patent No.: US 8,906,327 B2
(45) Date of Patent: Dec. 9, 2014

(54) PIPETTE TIP STACKING TRAY

(75) Inventors: Eric Williams, San Diego, CA (US); Hari Reddy, San Diego, CA (US)

(73) Assignee: Molecular Bioproducts, Inc., San Diego, CA (US)

( * ) Notice: Subject to any disclaimer, the term of this patent is extended or adjusted under 35 U.S.C. 154(b) by 0 days.

(21) Appl. No.: 13/082,998

(22) Filed: Apr. 8, 2011

(65) Prior Publication Data

US 2012/0257953 A1 Oct. 11, 2012

(51) Int. Cl.

*B01L 3/02* (2006.01)
*B01L 9/00* (2006.01)
*C12M 3/00* (2006.01)

(52) U.S. Cl.

CPC ............... *B01L 9/543* (2013.01); *B01L 3/0275* (2013.01); *B01L 2200/025* (2013.01)
USPC ..................... 422/564; 435/288.3; 435/288.4; 422/524

(58) Field of Classification Search

USPC .......................................................... 422/564
See application file for complete search history.

(56) References Cited

U.S. PATENT DOCUMENTS

D246,466 S 11/1977 Attree et al.
4,087,248 A * 5/1978 Miles ............................ 436/506
D276,071 S 10/1984 Malinoff
D302,207 S 7/1989 Matkovich
5,392,914 A 2/1995 Lemieux et al.
D359,126 S 6/1995 Hovatter
5,441,702 A 8/1995 Lemieux et al.
5,612,000 A 3/1997 Lemieux
5,642,816 A 7/1997 Kelly et al.
5,779,984 A 7/1998 Kelly et al.
D414,271 S 9/1999 Mendoza
D420,142 S 2/2000 Ballin et al.

(Continued)

OTHER PUBLICATIONS

European Patent Office, European Search Report, Application No. 12163587, Jul. 16, 2012 (4 pages).

(Continued)

*Primary Examiner* — Jill Warden
*Assistant Examiner* — Brittany Fisher
(74) *Attorney, Agent, or Firm* — Wood, Herron & Evans, LLP

(57) ABSTRACT

A stackable pipette tip tray is described. The pipette tip tray includes a deck having first and second opposing longitudinal side edges. A plurality of shaft apertures is arranged into a plurality of longitudinal rows on the deck. Each of the shaft apertures has a first size or shape configured to receive a shaft of a pipette tip. The deck also includes a plurality of tip apertures that is also arranged into a plurality of longitudinal rows such that at least one of the longitudinal rows of tip apertures is located between an adjacent pair of longitudinal rows of shaft apertures. Each of the plurality of tip apertures has a second size or shape, different from the first size or shape, and is configured to receive a distal tip end of a pipette tip when one tray of pipette tips is stacked above another tray of pipette tips. The plurality of longitudinal rows of shaft apertures is further arranged such that an outer one of the plurality of longitudinal rows of shaft apertures adjacent the first side edge of the deck is positioned closer to the first side edge than an outer one of the plurality of longitudinal rows of shaft apertures adjacent the second side edge of the deck is positioned relative to the second side edge.

12 Claims, 9 Drawing Sheets

(56) References Cited

U.S. PATENT DOCUMENTS

| | | | | |
|---|---|---|---|---|
| D420,743 | S | 2/2000 | Monks | |
| 6,019,225 | A * | 2/2000 | Kalmakis et al. | 206/563 |
| 6,164,449 | A | 12/2000 | Lahti | |
| 6,286,678 | B1 | 9/2001 | Petrek | |
| 6,405,870 | B1 | 6/2002 | Lahti et al. | |
| D461,554 | S | 8/2002 | Lafond et al. | |
| D463,863 | S | 10/2002 | Carlson et al. | |
| D464,734 | S | 10/2002 | Berna et al. | |
| D466,219 | S | 11/2002 | Wynschenk et al. | |
| D469,544 | S | 1/2003 | Lafond et al. | |
| 6,514,466 | B2 | 2/2003 | Labriola et al. | |
| D492,792 | S | 7/2004 | Kokaisel et al. | |
| D533,948 | S | 12/2006 | Schaub et al. | |
| D556,338 | S | 11/2007 | Coulling et al. | |
| D556,339 | S | 11/2007 | Coulling et al. | |
| D562,463 | S | 2/2008 | Berndt et al. | |
| D574,505 | S | 8/2008 | Muller-Cohn et al. | |
| D574,506 | S | 8/2008 | Monks | |
| D576,208 | S | 9/2008 | Quercetti | |
| D598,128 | S | 8/2009 | Pihl et al. | |
| D601,713 | S | 10/2009 | Lohn et al. | |
| D601,714 | S | 10/2009 | Lohn et al. | |
| D608,013 | S | 1/2010 | Coulling et al. | |
| D622,860 | S | 8/2010 | Karpiloff | |
| D632,404 | S | 2/2011 | Karpiloff | |
| D632,803 | S | 2/2011 | Motadel et al. | |
| D638,138 | S | 5/2011 | Wong | |
| D639,447 | S | 6/2011 | Karpiloff | |
| 2008/0053940 | A1* | 3/2008 | Whalen et al. | 211/134 |
| 2011/0300620 | A1* | 12/2011 | Belz et al. | 435/287.2 |

OTHER PUBLICATIONS

Quality Scientific Plastics, Product Catalog, QSP Pipette Tips & Tubes, Features and Benefits and Packaging Options (8 pages).

* cited by examiner 74
52
58
62
52
56
40
58
62
56
42
71
73
14
34
22
48
22
20
32
24

10b
10a
70
60
72

PIPETTE TIP STACKING TRAY

FIELD OF THE INVENTION

The present invention relates generally to pipette tip trays and, more particularly, to stackable pipette tip trays for use with pipette tips, including filter pipette tips.

BACKGROUND OF THE INVENTION

Disposable pipette tips are often packaged within trays that function to support and organize the pipette tips and to aid in the placement of one or more pipette tips onto a pipetter having one or more channels. These trays may be housed within a container or rack that is convenient for bench-top applications.

Often, the trays are either refillable, i.e., pipette tips may be reloaded into an empty tray, which may or may not be sterilized between uses, or disposable and replaceable with a filled tray. In either situation, multiple trays may be packaged together in a stack for storage convenience and for efficient reloading of a rack with a new filled tray of pipette tips after the previous tray is emptied of its pipette tips during use. However, the stacking of multiple trays containing pipette tips is not straightforward because the overall length of each pipette tip is often greater than the thickness of the tray. That is, the shafts of the pipette tips extend beyond the bottom of each tray. Simply stacking the trays would cause the distal tip ends of the pipette tips in an upper tray to fall within the lumens of the pipette tips in a lower tray. When an upper tray is then removed from the stack, the pipette tips of the lower tray may be ejected from the lower tray along with the upper tray. This defeats the organizational purposes and convenience of stackable trays.

While in some applications this may not present a problem, the known conventional stacking arrangements are not practical for stacking trays containing filter pipette tips. Filter pipette tips have a structure that is similar to standard pipette tips but further include a semi-porous structure within the lumen of the pipette tip. As a result, the distal tip ends of the filter pipette tips in an upper tray cannot fall within the lumens of the filter pipette tips in a lower tray without interfering and/or damaging the semi-porous structure and/or the pipette tip. Because known alternative arrangements for stacking pipette tip trays have not provided satisfactory solutions for filter pipette tips, i.e., stacking is neither efficient with respect to storage capability nor conducive to the laboratory environment where technicians often wear gloves with diminished dexterity or handling by laboratory robotics, there remains a need for a pipette tip tray that is capable of supporting pipette tips, particularly filter pipette tips, and that is stackable in a simple but efficient manner for use with a pipette tip rack.

SUMMARY OF THE INVENTION

The present invention overcomes the foregoing problems and other shortcomings, drawbacks, and challenges of stacking conventional pipette tip trays for use with a storage container or rack. While the invention will be described in connection with certain embodiments, it will be understood that the invention is not limited to these embodiments. To the contrary, this invention includes all alternatives, modifications, and equivalents as may be included within the spirit and scope of the present invention.

In one illustrative embodiment, the present invention is directed to a stackable pipette tip tray that includes a deck with first and second opposing longitudinal side edges. A plurality of shaft apertures is arranged into a plurality of longitudinal rows on the deck. Each of the shaft apertures has a first size or shape that is configured to receive a shaft of a pipette tip. The deck also includes a plurality of tip apertures that is also arranged into a plurality of longitudinal rows. At least one of the longitudinal rows of tip apertures is located between an adjacent pair of longitudinal rows of shaft apertures. Each of the plurality of tip apertures has a second size or shape that is different from the first size or shape of the shaft apertures and is configured to receive a distal tip end of a pipette tip when one tray of pipette tips is stacked above another tray of pipette tips. The plurality of longitudinal rows of shaft apertures are arranged such that an outer one of the plurality of longitudinal rows of shaft apertures adjacent to a first side edge of the deck is positioned closer to the first side edge than an outer one of the plurality of longitudinal rows of shaft apertures adjacent to a second side edge of the deck is positioned relative to the second side edge.

Another illustrative embodiment of the invention is directed to a stack of at least first and second pipette tip trays. Each of the first and second pipette tip trays includes a deck with first and second opposing longitudinal side edges. A plurality of shaft apertures is arranged into a plurality of longitudinal rows on each respective deck. Each of the shaft apertures has a first size or shape configured to receive a shaft of a pipette tip. Each respective deck also includes a plurality of tip apertures, each having a second size or shape that is different from the first size or shape of the shaft apertures and is configured to receive a distal tip end of a pipette tip when one tray of pipette tips is stacked above another tray of pipette tips and arranged into a plurality of longitudinal rows of tip apertures. The stack is configured such that the first pipette tip tray is positioned above, and is rotated relative to, the second pipette tip tray. The first side edge of the first pipette tray is vertically aligned with the second side edge of the second pipette tip tray, and the second side edge of the first pipette tray is vertically aligned with the first side edge of the second pipette tip tray. Furthermore, the plurality of shaft apertures of the first pipette tip tray is vertically aligned with the plurality of tip apertures of the second pipette tip tray.

Yet another illustrative embodiment of the invention is directed to a stack of at least first and second pipette tip trays. Each of the first and second pipette tip trays includes a deck with first and second opposing longitudinal side edges. A plurality of shaft apertures is arranged into a plurality of longitudinal rows on each respective deck with each of the plurality of shaft apertures having a first size or shape that is configured to receive a shaft of a pipette tip. Each respective deck also includes a plurality of tip apertures, arranged into a plurality of longitudinal rows, and each tip aperture having a second size or shape that is different from the first size or shape of the shaft apertures and is configured to receive a distal tip end of a pipette tip when one tray of pipette tips is stacked above another tray of pipette tips. At least one longitudinal row of tip apertures is located between an adjacent pair of longitudinal rows of shaft apertures. The plurality of longitudinal rows of shaft apertures on each respective deck are arranged such that an outer one of the plurality of longitudinal rows of shaft apertures adjacent to a first side edge of the respective deck is positioned closer to the first side edge than an outer one of the plurality of longitudinal row of shaft apertures adjacent to a second side edge of the respective deck is positioned relative to the second side edge. The stack is further configured such that the first pipette tip tray is positioned above, and is rotated relative to, the second pipette tip tray. The first side edge of the first pipette tray is vertically aligned with the second side edge of the second pipette tip tray, and the second side edge of the first pipette tray is vertically aligned with the first side edge of the second pipette tip tray.

In another illustrative embodiment, the invention is directed to a method of stacking at least first and second pipette tip trays. Each of the first and second pipette tip trays includes a deck with first and second side opposing lateral side edges. A plurality of shaft apertures is arranged on each respective deck into a plurality of longitudinal rows and each shaft aperture has a first size or shape that is configured to receive shafts of a plurality of pipette tips. A plurality of tip apertures is arranged into a plurality of longitudinal rows on each respective deck. Each of the plurality of tip apertures has a second size or shape that is different from the first size or shape of the shaft apertures and is configured to receive a distal tip end of a pipette tip when one tray of pipette tips is stacked above another tray of pipette tips. The method includes positioning a first pipette tip tray above a second pipette tip tray. The first pipette tip tray is rotated relative to the second pipette tip tray so that the first side edge of the first pipette tip tray vertically aligns with the second side edge of the second pipette tip tray, and the second side edge of the first pipette tip tray vertically aligns with the first side edge of the second pipette tip tray. The first and second pipette tip trays are advanced together such that the distal tip ends of the plurality of pipette tips residing within the plurality of shaft apertures of the first pipette tip tray are received by the plurality of tip apertures of the second pipette tip tray.

The above and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF THE INVENTION

Figure 1:
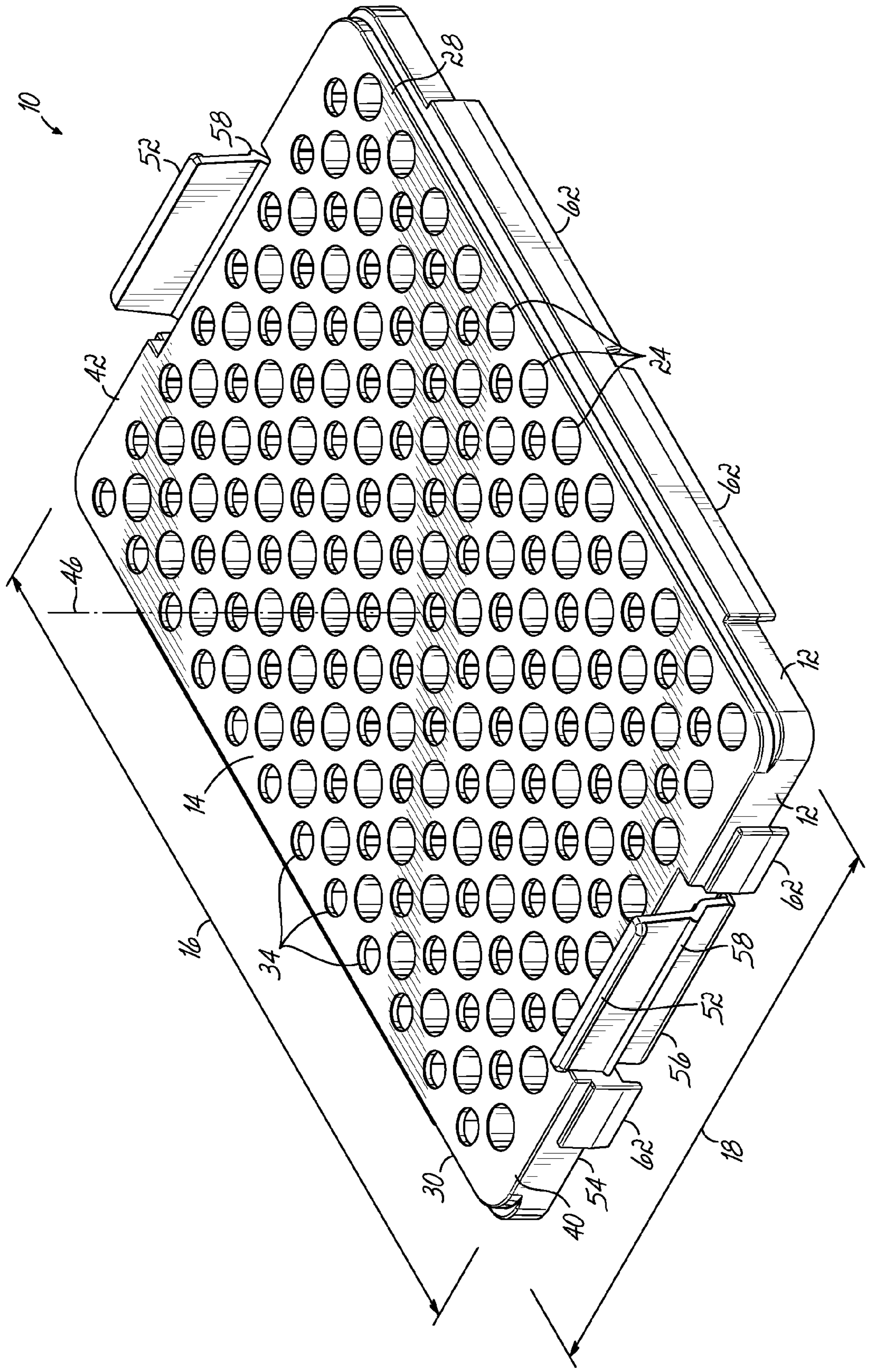
FIG. 1 is a perspective view of a stackable pipette tip tray in accordance with one embodiment of the present invention.
Figure 2:
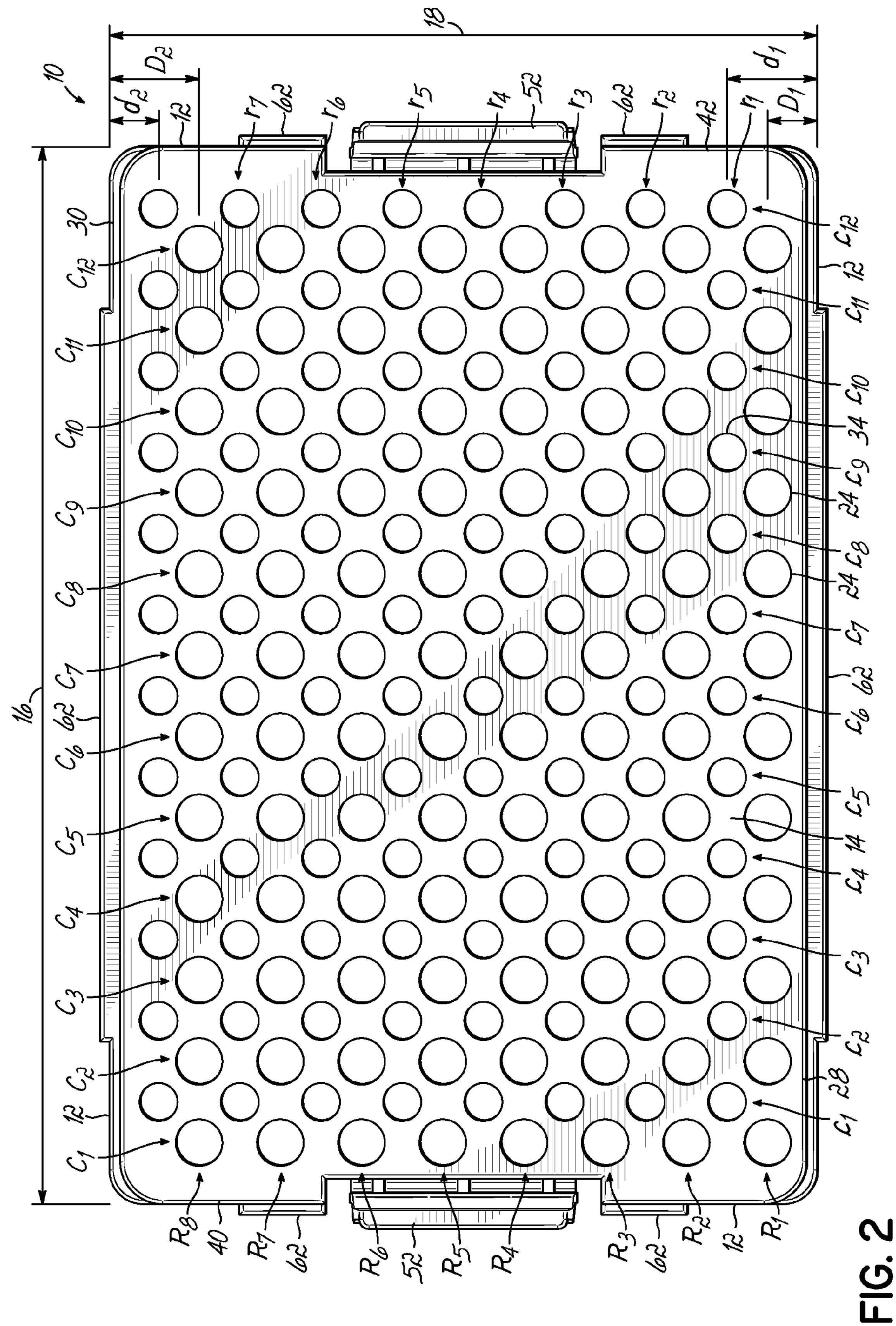
FIG. 2 is a top view of the pipette tip tray of FIG. 1.
Figure 3:
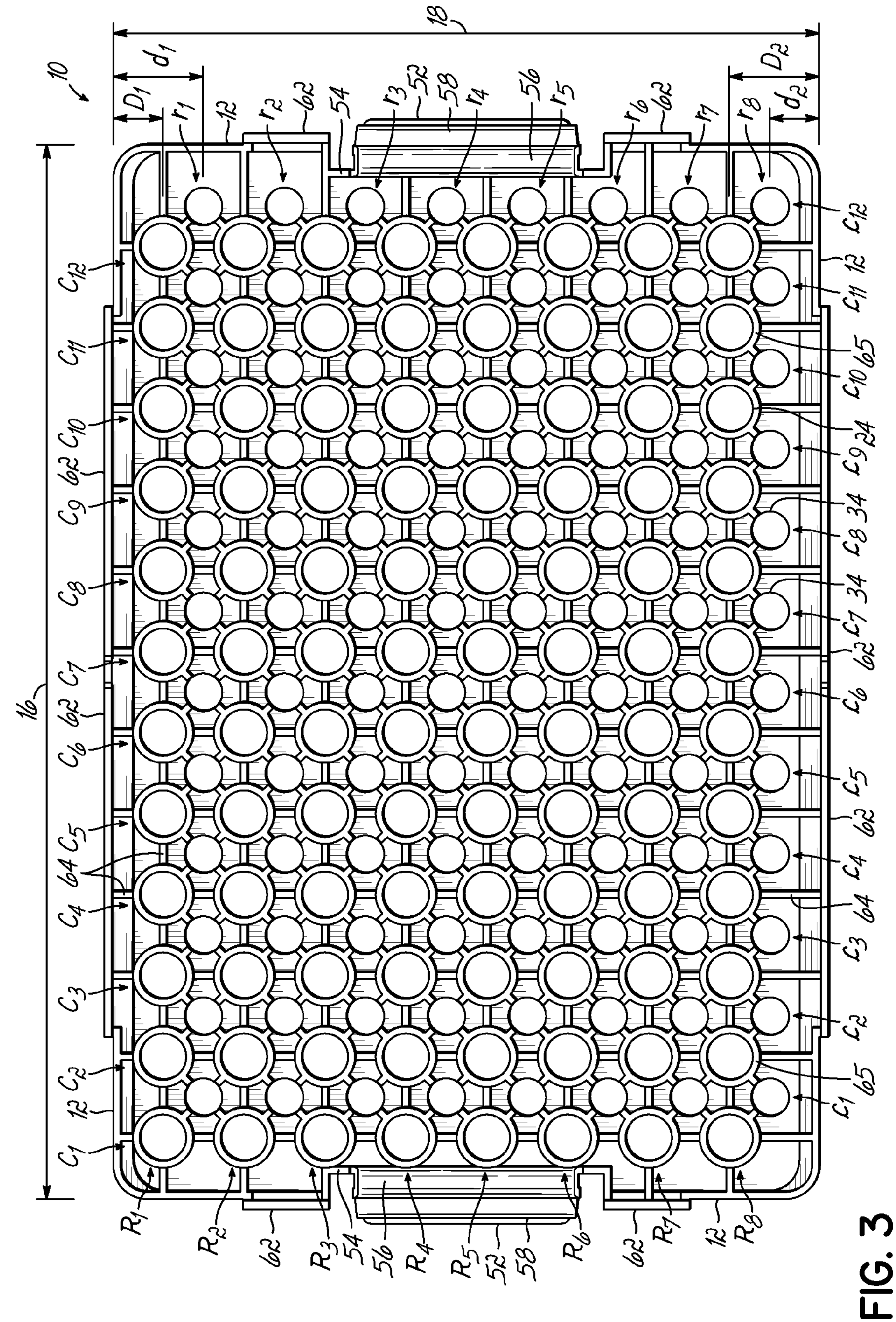
FIG. 3 is a bottom view of the pipette tip tray of FIG. 1.

Turning now to the figures, and particularly to FIGS. 1-3, a first embodiment of a pipette tip tray ("tray" 10) is shown and described in detail. The tray 10 includes opposing end-walls and opposing sidewalls 12 and a planar deck 14 having a longitudinal dimension (arrow 16) and a lateral dimension (arrow 18). The deck 14 includes a first set of apertures having a first size or shape that is configured to receive the shaft 20 (FIG. 4) of a pipette tip 22 (FIG. 4) ("shaft apertures" 24). The pipette tips 22 may be of any desired size, but are particularly illustrated in FIGS. 1-7 for use with medium sized pipette tips, e.g., 20 μL to 300 μL sized pipette tips.

The shaft apertures 24 are arranged into a plurality of rows along the longitudinal dimension and such that the outer row of shaft apertures 24 that is adjacent to a first longitudinal side edge 28 of the deck 14 is positioned closer to the first longitudinal side edge 28 than the outer row of shaft apertures 24 adjacent the second longitudinal side edge 30 of the deck 14 is positioned relative to the second longitudinal side edge 30. Said another way, and referring to FIG. 2, the shaft apertures 24 are arranged into n number of longitudinal rows ("$R_n$"), where n is any integer greater than or equal to 2 and, specifically in one embodiment herein, equal to 8. The rows of shaft apertures 24 are arranged such that $R_1$ is adjacent the first longitudinal side edge 28 and $R_8$ is adjacent the second longitudinal side edge 30. The distance between the first longitudinal side edge 28 of the deck 14 and $R_1$ ("$D_1$") is less than the distance between the second longitudinal side edge 30 of the deck 14 and $R_8$ ("$D_2$"). For the sake of simplicity, $D_1$ and $D_2$ are measured from the midpoint of the shaft apertures 24 within the respective row to the respective side edges 28, 30 of the deck 14.

One of ordinary skill in the art will readily appreciate that the number of shaft apertures 24 comprising each longitudinal row is not limited to the 12 shaft apertures of the illustrated embodiment in FIG. 1. Instead, the number of shaft apertures 24 in each row may be altered to the particular intended use or as otherwise desired.

A second set of apertures, having a second size or shape that is different from the first size or shape of the shaft apertures 24 and configured to receive the distal tip end 32 (FIG. 4) of the pipette tip 22 (FIG. 4) ("tip apertures" 34), is positioned on the deck 14 into a plurality of longitudinal rows and at least one of the longitudinal rows of tip apertures 34 is spaced between an adjacent pair of longitudinal rows of shaft apertures 24.

In one embodiment, the shaft apertures 24 and the tip apertures 34 are both circular, with the tip apertures 34 having a smaller diameter than the diameters of the shaft apertures 24. Alternatively, the tip apertures 34 may have a different shape or configuration as compared to the shape or configuration of the shaft apertures 24. For example, and by way of illustration only, the shaft apertures 24 may be circular in shape while the tip apertures 34 may be formed in the shape of a diamond, triangle, oval, cross or any other suitable different shape for receiving the distal tip ends 32 of the pipette tips 22.

As shown in FIGS. 1-3, an outer row of tip apertures 34 adjacent to the first longitudinal side edge 28 of the deck 14 is positioned farther from the first longitudinal side edge 28 than the outer row of tip apertures 34 adjacent the second longitudinal side edge 30 of the deck 14 is positioned relative to the second longitudinal side edge 30. Again, said another way, and referring to FIG. 2, the tip apertures 34 are arranged into n number of longitudinal rows ("$r_n$"), where n is any integer greater than or equal to 2 and, specifically in one embodiment herein, equal to 8. The rows of tip apertures 34 are arranged such that $r_1$ is adjacent the first longitudinal side edge 28 and $r_8$ is adjacent the second longitudinal side edge 30. The distance between the first longitudinal side edge 28 of the deck 14 and $r_1$ ("$d_1$") is greater than the distance between the second longitudinal side edge 30 of the deck 14 and $r_8$ ("$d_2$").

For the sake of simplicity, $d_1$ and $d_2$ are measured from the midpoint of the tip apertures 34 within the respective row to the respective side edges 28, 30 of the deck 14.

While the number of tip apertures 34 comprising the longitudinal rows may vary, there is particular benefit to having the same number of tip apertures 34 comprising each row as the number of shaft apertures 24 comprising those longitudinal rows.

It will be readily appreciated that the shaft apertures 24 and the tip apertures 34 may also align into respective columns (illustrated herein as $C_1$ to $C_{12}$ and $c_1$ to $c_{12}$, respectively), wherein each column $C_n$, $c_n$ extends along the lateral dimension. Thus, the same relationship between the lateral edges of the deck 14 to adjacent lateral columns $C_n$, $c_n$ may exist for both the shaft apertures 24 and the tip apertures 34. That is, the column $C_1$ of shaft apertures 24 adjacent a first lateral outer edge 40 of the deck 14 is positioned closer to the first lateral outer edge 40 than the column $C_{12}$ of shaft apertures 24 adjacent to a second lateral edge 42 of the deck 14 is positioned relative to the second lateral edge 42. Because columns $c_n$ of tip apertures 34 are spaced between adjacent pairs of columns $C_n$ of shaft apertures 24, the opposite would be true for columns $c_n$ of tip apertures 34, e.g., the column $c_1$ of tip apertures 34 adjacent the first lateral outer edge 40 of the deck 14 is positioned farther from the first lateral outer edge 40 than the column $c_{12}$ of tip apertures 34 adjacent to the second lateral edge 42 of the deck 14 is positioned relative to the second lateral edge 42. Accordingly, the shaft apertures 24 are rotationally symmetric with the tip apertures 34 about a centrally-disposed axis 46 that extends orthogonal from the deck 10. The rotational symmetry is described in greater detail below with reference to the method of stacking trays.

The tray 10 may be molded as a unitary structure from a suitable polymeric material. The shaft apertures 24 are sized and shaped to accommodate a particular size pipette tip 22 (FIG. 4) and to reduce movement of the pipette tip 22 (FIG. 4) within the shaft aperture 24 when seating the pipetter shaft (not shown) with the enlarged hub 48 of the pipette tip 22. The tip apertures 34 are sized to receive the distal tip end 32 (FIG. 4) and a distal portion of the shaft 20 (FIG. 4) of the pipette tip 22 (FIG. 4) and to move relative thereto without interference that would otherwise hinder removal of the pipette tip 22 (FIG. 4) from the tray 10.

Figure 4:
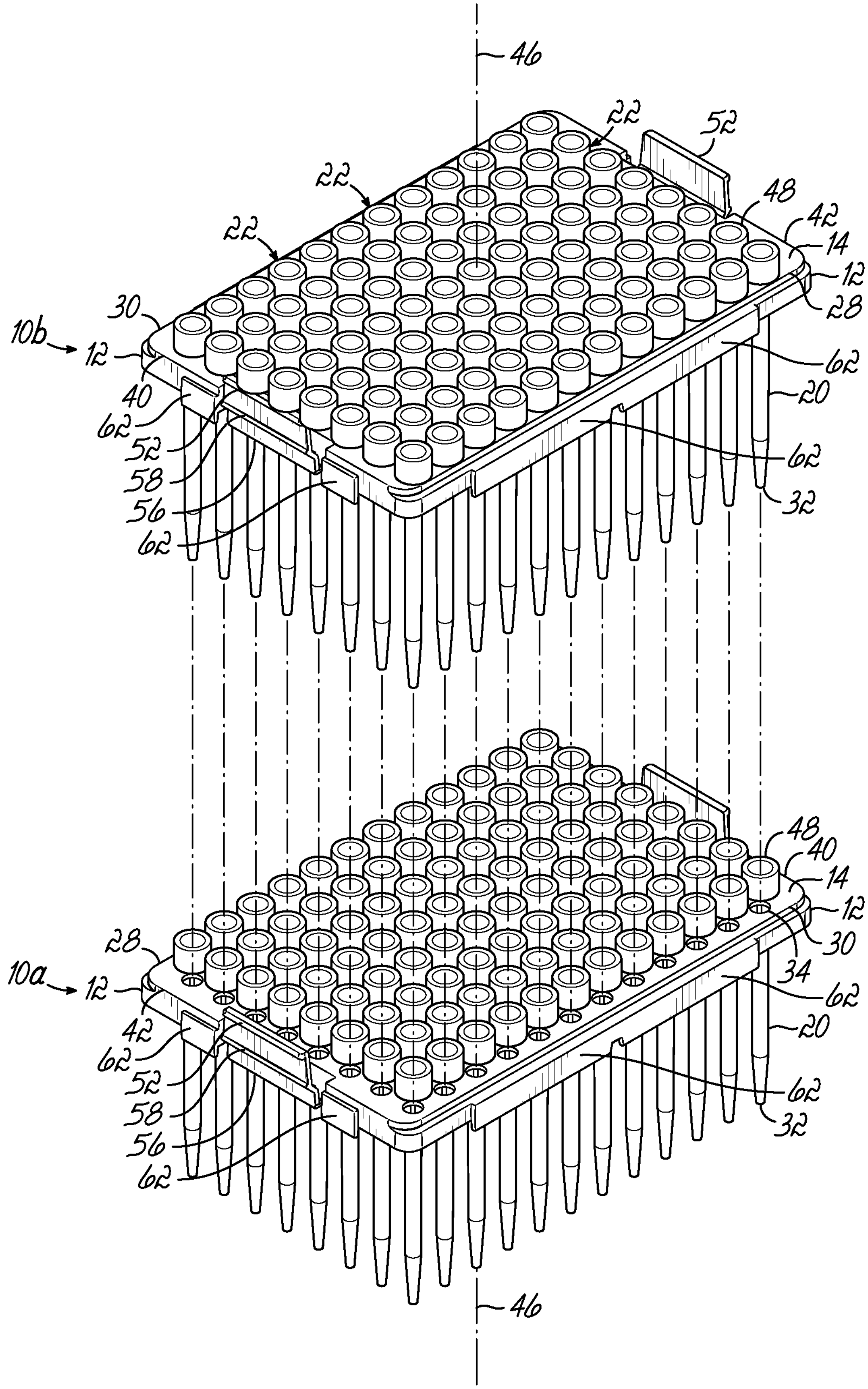
FIG. 4 illustrates one exemplary method of stacking two pipette tip trays that are both similar to the pipette tip tray of FIG. 1 and where each pipette tip tray includes a plurality of pipette tips.

Various ancillary features may be included in the molded unitary tray structure, including, for example, combinations of locking tabs, handles, and supports. In the illustrative embodiment, the tray 10 includes two handles 52, one on each of the lateral outer edges 40, 42 of the deck 14, that extend upwardly from the deck 14 to provide a contact point for handling the tray 10 without directly handling the pipette tips 22 (FIG. 4). The particular illustrative embodiment of handles 52 shown are also configured to serve as a hinged tab. Accordingly, the handles 52 are connected to a bottom portion 54 of the tray 10 by a hinge strap 56. The handles 52 further include a snap tab 58 configured to releasably secure the tray 10 into rack, i.e., a storage container 60 (FIG. 6), as will be described in greater detail below. The end-walls and sidewalls 12 at the lateral outer edges 40, 42 and the longitudinal side edges 28, 30 also include stand supports 62, which extend downwardly from the deck 14 for supporting the tray 10 within the storage container 60 (FIG. 6) as provided in detail below. Additionally, or alternatively, the handles may be included on the longitudinal outer edges 28, 30 if so desired.

In FIG. 3, a bottom view of the tray 10 is shown to include ribs 64 extending longitudinally and laterally across the tray 10 and, optionally, radially between the shaft apertures 24 and the tip apertures 34. The shaft apertures 24 may be associated with a sleeve 65 that is aligned with the respective aperture 24. As shown, the ribs 64 and the sleeves 65 are contiguous; however, this is not required. Indeed, the ribs 64 are not required but use of these ribs 64 provides additional strength and stability to the tray 10 to resist a downwardly-directed force that may be applied when inserting the pipetter (not shown) into the enlarged hub 22 (FIG. 4) of the pipette tip (FIG. 4). Furthermore, the particular arrangement of the ribs 64 may vary to accommodate a desired aperture arrangement or to provide a desired level of rigidity to the tray 10. The sleeves 65, which are only shown to extend downwardly from the deck 14, may also extend above the deck 14 to further support the shafts 20 extending therethrough.

Figure 5:
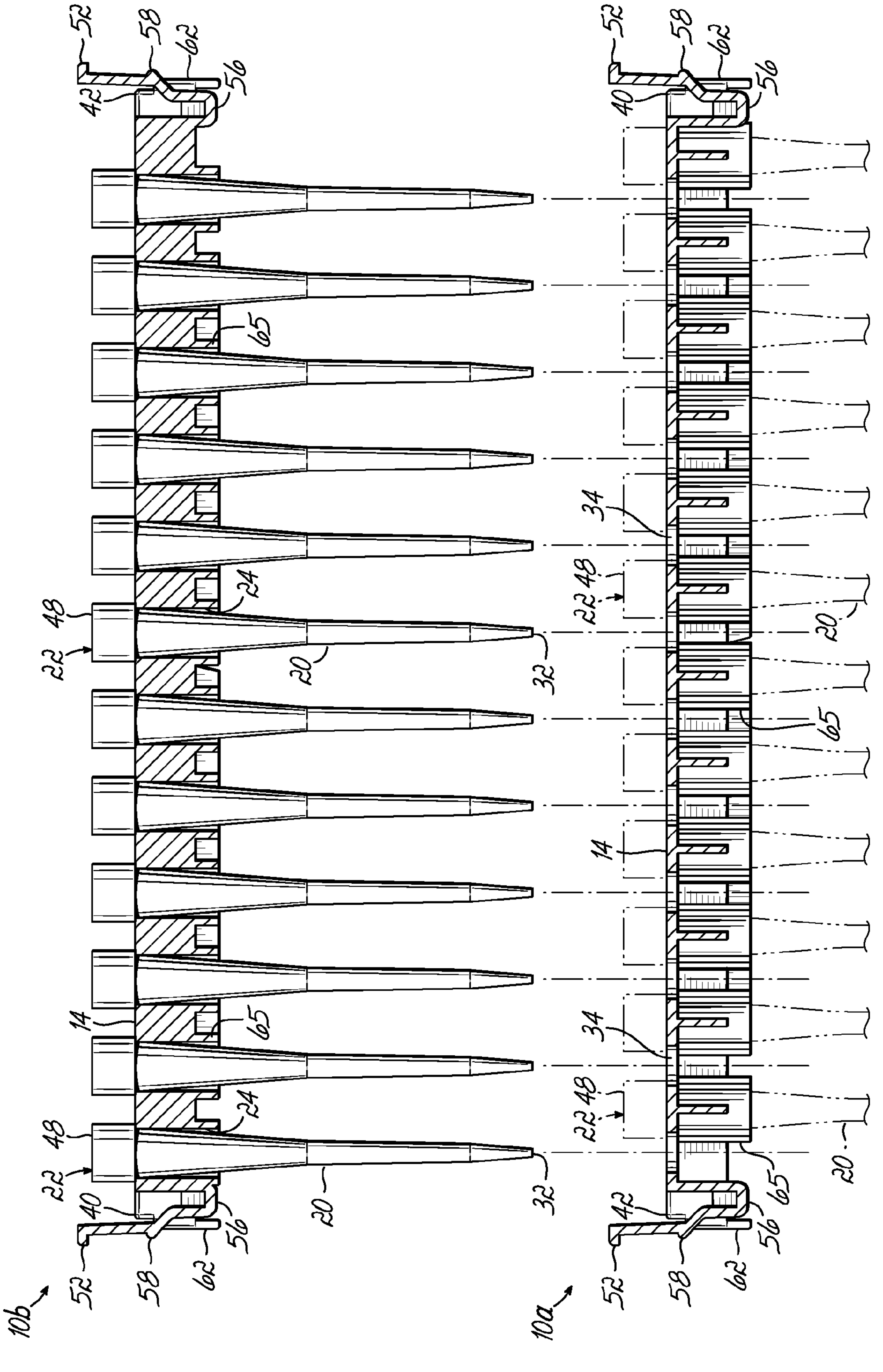
FIG. 5 is a cross-sectional view of the method of stacking the two pipette tip trays shown in FIG. 4.

Turning now to FIGS. 4 and 5, one method of stacking two trays 10*a*, 10*b*, each loaded with a plurality of pipette tips 22 is described with greater detail and where the trays 10*a*, 10*b* are constructed in a manner that is similar to the tray 10 of FIG. 1. While these trays are referred to herein as the top tray 10*b* and the bottom tray 10*a*, it will be readily understood that this is for illustrative convenience only and that the stacking of trays in not limited to two trays at a time. The top and bottom trays 10*b*, 10*a* each include a plurality of pipette tips 22 that are received by and extend through each of the shaft apertures 24 such that the shafts 20 of the pipette tips 22 extend beyond the end-walls and sidewalls 12. As is more clearly shown in the bottom tray 10*a* in FIG. 4, the tip apertures 34 are vacant prior to stacking.

Before stacking, the top tray 10*b* is rotated 180° about the centrally-disposed orthogonal axis 46 with respect to the bottom tray 10*a*, as shown in FIG. 4. In this way, the distal tip ends 32 of the pipette tips 22 within the top tray 10*b* will vertically align with the tip apertures 34 of the bottom tray 10*a*. This is perhaps more clearly shown in the cross-sectional view of FIG. 5. Again, the distal tip ends 32 of the pipette tips 22 that reside in the shaft apertures 24 of the top tray 10*b* are positioned to be directly and vertically above and aligned with the tip apertures 34 of the bottom tray 10*a*. As the top tray 10*b* is moved toward and onto the bottom tray 10*a*, the distal tip ends 32 of the pipette tips 22 of the top tray 10*b* enter and extend through the tip apertures 34 of the bottom tray 10*a*. Movement of the trays 10*a*, 10*b* continues until the bottom portion 54 (FIG. 3) of the top tray 10*b* rests atop the enlarged hubs 48 of the pipette tips 22 of the bottom tray 10*a*. While not shown, it would be permissible to include one or more spires extending upwardly from the deck 14 and on which the bottom portion 54 (FIG. 3) is positioned.

Figure 6:
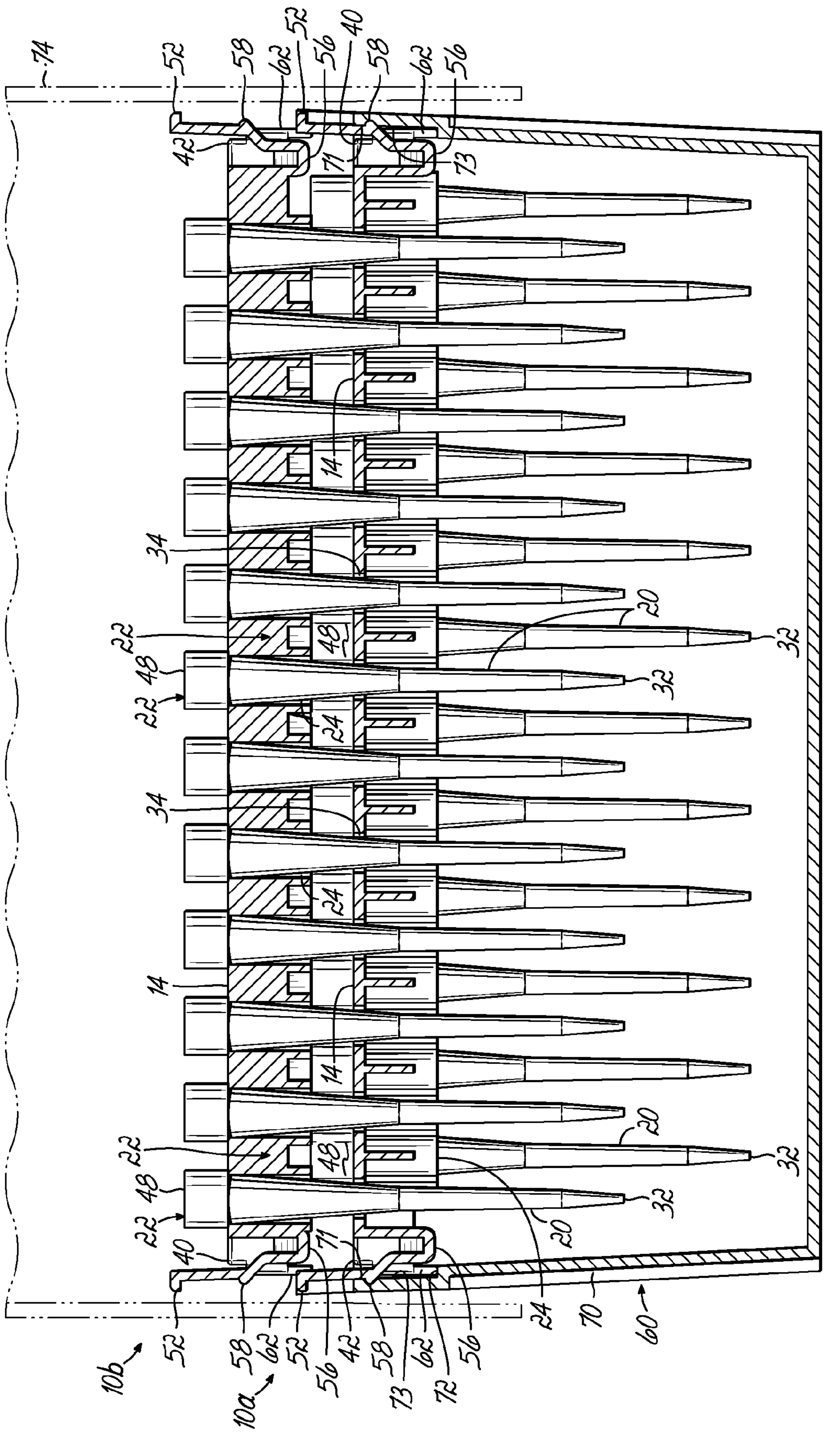
FIG. 6 is a side-elevational view of a pipette tip rack and the stack of two pipette tip trays of FIG. 4.

In the stacked configuration shown in FIG. 6, the pipette tips 22 of the top tray 10*b* are staggered with respect to the pipette tips 22 of the bottom tray 10*a*. It will be readily appreciated that despite the staggering of the pipette tips 22, the end-walls and sidewalls 12 of the top and bottom trays 10*b*, 10*a* are vertically aligned and not themselves staggered. More specifically, the first longitudinal side edge 28 of the top tray 10*b* is in vertical, planar alignment with the second longitudinal side edge 30 of the bottom tray 10*a* and the second longitudinal side edge 30 of the top tray 10*b* is in vertical, planar alignment with the first longitudinal side edge 28 of the bottom tray 10*a*. The same relative arrangement is also shown for the respective first and second lateral outer edges 40, 42. In this way, the footprint of the stacked trays 10*a*, 10*b* is minimized.

Figure 7:
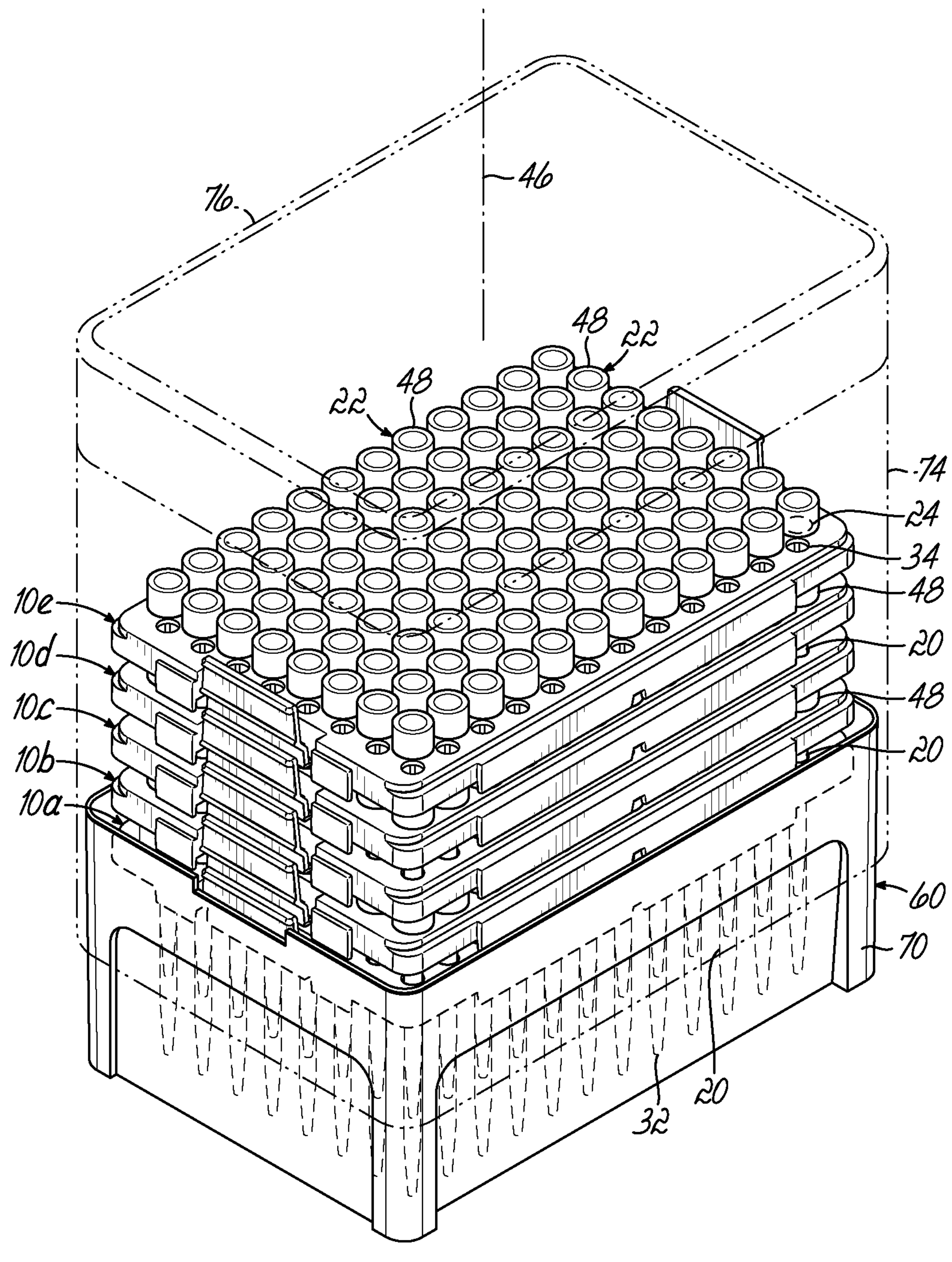
FIG. 7 illustrates a pipette tip rack and a stack of five pipette tip trays.

With reference now to FIGS. 6 and 7, one method of loading a tray 10 into a container 60, also known as a rack, is described in detail. The container 60 is particularly useful for temporary storage and use at the bench-top while a separate stack of trays is available for long terms storage. The container 60 may be constructed from a molded polymer and includes a base portion 70 that is sufficiently tall to receive the distal tip ends 32 of the pipette tips 22 that are extending downwardly from the end-walls and sidewalls 12 of the tray 10 positioned in the container 60. The container 60 may also include at least one shelf 72 therein for supporting the stand supports 62 of the tray 10*a*.

The snap tab 58 of the hinged handles 52 of a first tray 10*a* are received by a recess 73 within the inner edge of the base portion 70 to, at least temporarily, retain the first tray 10*a* within the container 60 by a retention tab 71. To remove the first tray 10*a*, the hinged handles are inwardly biasing such that the snap tabs 58 are released from the recesses 73 and biased over the retention tab 71. The first tray 10*a* is then lifted upwardly by the same handles 52. It will be appreciated that in some embodiments the hinged handles 52 may be of sufficient height as to sit flush with a top edge of the container 60 for access and/or clear the height of the hubs 48 of the pipette tips 22.

As shown in FIG. 7, after an empty tray (not shown) is removed from the container 60, a new tray loaded with a plurality of pipette tips 22 may be loaded into the container 60. In accordance with one embodiment, reloading the container 60 includes transfer of a tray from a stack of trays stored within a storage cover sleeve 74, which is illustrated here as a stack of five trays 10*a*-10*e*. The sleeve 74 includes an open end that is configured to be received by the container 60 for reloading the container 60 with the bottom-most tray 10*a* of pipette tips 22 and a push plate 76 on an end that opposes the open end. The push plate 76 is configured to be pressed downwardly into the sleeve 74 and contact the enlarged hubs 48 of the top-most tray 10*e*. While various embodiments of storage cover sleeves are possible, the particular illustrated embodiment includes tapered walls that provide frictional fit with at least the bottom-most tray 10*a* or otherwise configured to retain the stack within the sleeve 74.

It will be readily appreciated that each tray 10*a*-10*e* within the stack is rotated about the centrally-disposed orthogonal axis 46 with respect to the tray 10*a*-10*d* immediately above and/or below the respective tray such that the distal tip ends 32 align with the tip apertures 34 of the tray 10*a*-10*d* immediately below the respective tray. Furthermore, the end-walls and sidewalls 12 of all trays 10*a*-10*e* within the stack are in vertical, planar alignment, i.e., the end-walls and sidewalls 12 lie in respective common vertical planes.

To dispense the bottom-most tray 10*a* into the container 60, the user presses downwardly on the push plate 76 of the sleeve 74 to advance the push plate 76 into the sleeve 74 and to contact the top-most tray 10*e*. Continued downward pressure on the push plate 76 transmits the force through the stack of trays 10*a*-10*e* to the bottom-most tray 10*a*. With sufficient force transferred, the bottom-most tray 10*a* overcomes the frictional fit retaining the bottom-most tray 10*a* within the sleeve 74, is ejected from the sleeve 74, and is received into the container 60. Still further pressure causes the snap tab 58 of each hinged handle 52 to bias over the retention tab 71 and then automatically bias outwardly to be received by the respective recess 73. The remaining trays 10*b*-10*e* remain within the sleeve 74 are indexed or shifted downward by one position and remain in this position until the tray 10*a* is empty and a new tray is required.

Figure 8:
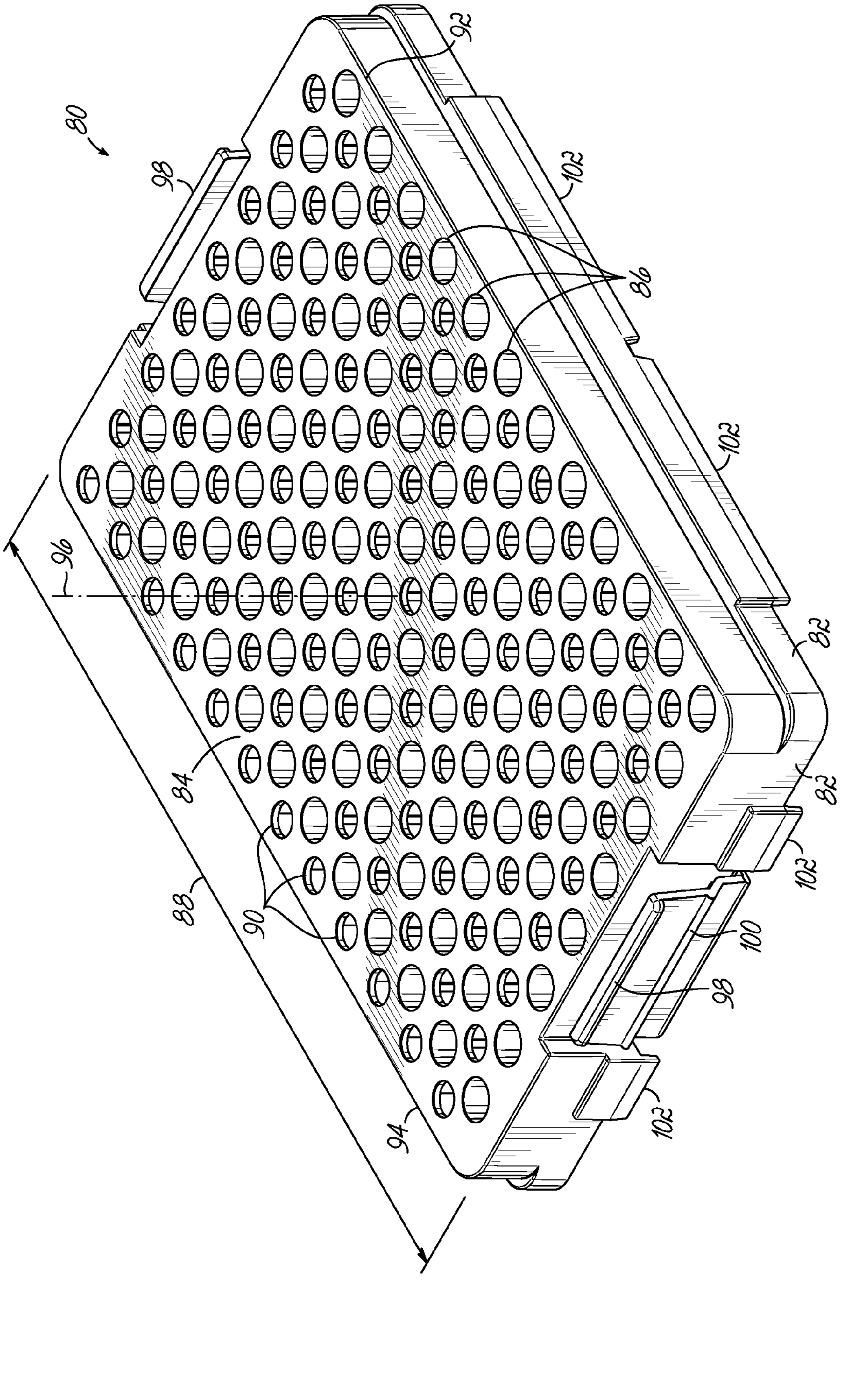
FIG. 8 is a perspective view of a stackable pipette tip tray in accordance with another embodiment of the present invention.

FIG. 8 illustrates a pipette tip tray 80 in accordance with another embodiment of the invention for use with a smaller volume pipette tip 22, e.g., 1 μL to 30 μL volume pipette tips. The tray 80 is similar to the tray 10 of FIG. 1 and thus includes opposing end-walls and opposing sidewalls 82 and a planar deck 84 having shaft apertures 86 arranged into a plurality of rows along a longitudinal dimension 88 and tip apertures 90 also arranged into a plurality of rows along a longitudinal dimension 88. The rows of shaft apertures 86 are arranged as described previously, namely, an outer row of shaft apertures 86 adjacent to a first longitudinal side edge 92 of the deck 84 is positioned closer to the first longitudinal side edge 92 than an outer row of shaft apertures 86 adjacent to a second longitudinal side edge 94 of the deck 84 is positioned relative to the second longitudinal side edge 94. Likewise, rows of tip apertures 90 are also arranged as described previously, namely, an outer row of tip apertures 90 adjacent to the first longitudinal side edge 92 of the deck 84 is positioned farther from the first longitudinal side edge 92 than an outer row of tip apertures 90 adjacent to the second longitudinal side edge 94 of the deck 84 is positioned relative to the second longitudinal side edge 94. Further, the shaft apertures 86 are rotationally symmetric with the tip apertures 90 about a centrally-disposed orthogonal axis 96. The tray 80 further includes hinged handles 98 having snap tabs 100 and stand supports 102, much like the tray 10 of FIG. 1.

However, the height of the sidewalls 82 of the tray 80 is greater than the length of the sidewalls 12 of the tray 10 (FIG. 1). Because the illustrated tray 80 is configured to store smaller volume pipette tips 22, the longer sidewalls 82 of the tray 80 shield and stabilize the shafts 20 of the smaller pipette tips 22 within the tray 80.

Figure 9:
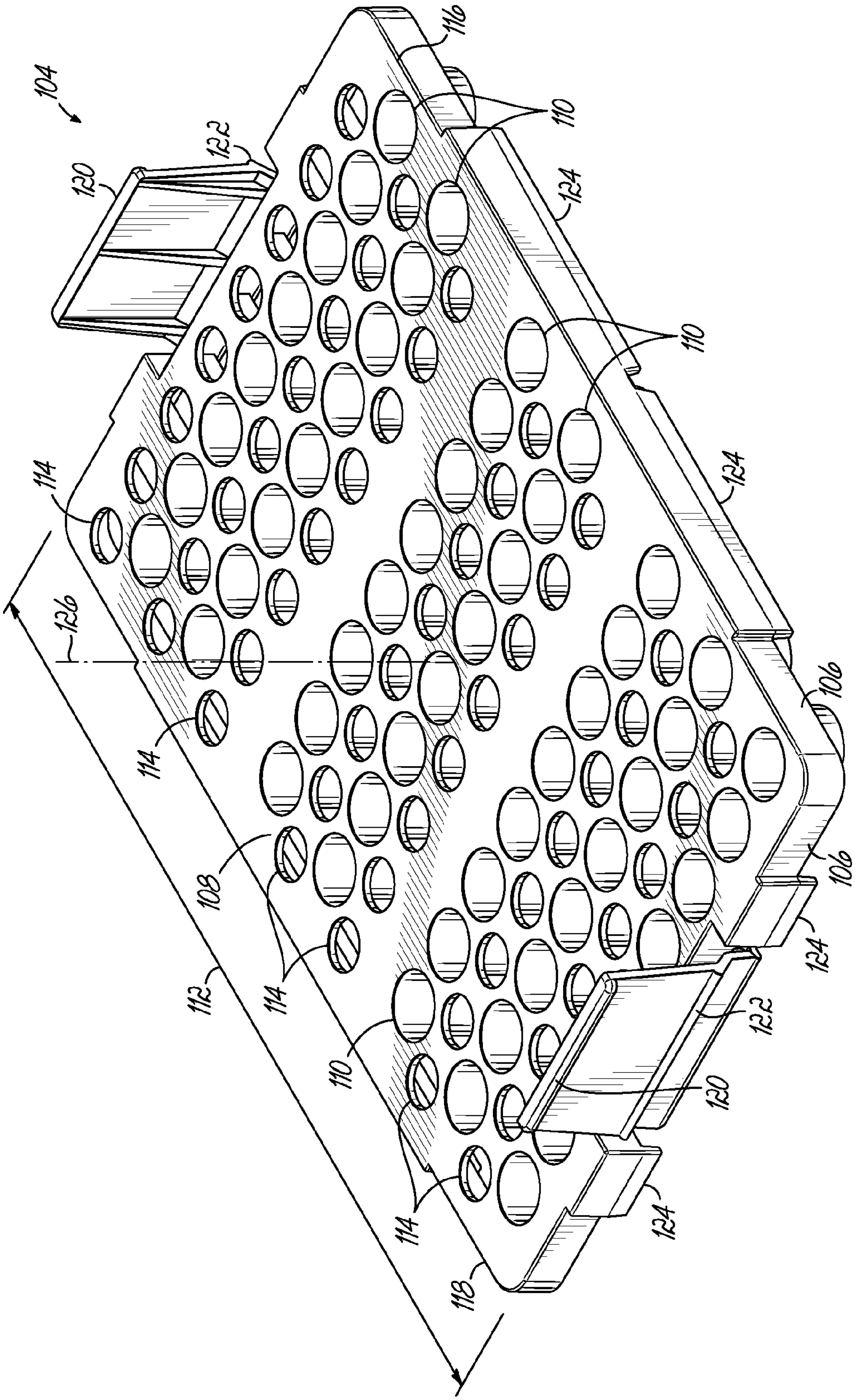
FIG. 9 is a perspective view of a stackable pipette tip tray in accordance with yet another embodiment of the present invention.

FIG. 9 illustrates a pipette tip tray 104 in accordance with another embodiment of the invention for use with a larger volume pipette tip 22, e.g., 1250 μL volume pipette tips. The tray 104 is similar to the trays 10 and 80 of FIGS. 1 and 8, respectively, and thus includes opposing end-walls and opposing sidewalls 106 and a planar deck 108 having shaft apertures 110 arranged into a plurality of rows along a longitudinal dimension 112. The deck 108 also includes tip apertures 114 arranged into a plurality of rows along a longitudinal dimension 112. The rows of shaft apertures 110 are arranged as described previously, namely, an outer row of shaft apertures 110 adjacent to a first longitudinal side edge 116 of the deck 108 is positioned closer to the first longitudinal side edge 116 than an outer row of shaft apertures 110 adjacent to a second longitudinal side edge 118 of the deck 108 is positioned relative the second longitudinal side edge 118. Likewise, the rows of tip apertures 114 are arranged such that an outer row of tip apertures 114 adjacent to the first longitudinal side edge 116 of the deck 108 is positioned farther from the first longitudinal side edge 116 than an outer row of tip apertures 114 adjacent to the second longitudinal side edge 118 of the deck 108 is positioned relative the second longitudinal side edge 118. The tray 104 further includes hinged handles 120 having snap tabs 122 and stand supports 124, much like the trays 10 and 80 of FIGS. 1 and 8, respectively.

It will be readily appreciated that the rows of shaft apertures 110 and the tip apertures 114 are discontinuous in the present embodiment, i.e., that the distance between successive apertures 110, 114 within their respective row is not equal, or constant, throughout the row. Yet, the arrangement of the shaft apertures 110 maintains a rotational symmetry about a centrally-disposed orthogonal axis 126 with the tip apertures 114. Accordingly, various arrangements and patterns of the shaft and tip apertures 110, 114 are possible and should not be limited to the specific embodiments illustrated herein.

Furthermore, it will be readily appreciated that the hinged handles 120 of the tray 104 are longer than the handles 52, 98 of the trays 10, 80 of FIGS. 1 and 8, respectively. These longer hinged handles 120 are sized to sit flush with the top edge of the container 60.

While the present invention has been illustrated by a description of various embodiments, and while these embodiments have been described in some detail, they are not intended to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with methods of practicing the present invention as currently known. However, the invention itself should only be defined by the appended claims.

What is claimed is:

1. A stackable pipette tip tray having a deck with first and second opposing longitudinal side edges each having a longitudinal dimension and first and second opposing lateral outer edges each having a lateral dimension, with the longitudinal dimension being greater than the lateral dimension, comprising:

a plurality of shaft apertures, each of the plurality of shaft apertures having a first size or shape configured to receive a shaft of a pipette tip, the plurality of shaft apertures arranged into a plurality of longitudinal rows on the deck between the first and second longitudinal side edges; and a plurality of tip apertures, each of the plurality of tip apertures having a second size or shape that is different from the first size or shape and configured to receive a distal tip end of a pipette tip, and the plurality of tip apertures being arranged into a plurality of longitudinal rows on the deck with at least one of the plurality of longitudinal rows of tip apertures being located between an adjacent pair of longitudinal rows of shaft apertures, wherein an outer one of the plurality of longitudinal rows of shaft apertures adjacent the first longitudinal side edge is positioned closer to the first longitudinal side edge than an outer one of the plurality of longitudinal rows of shaft apertures adjacent the second longitudinal side edge is positioned relative to the second longitudinal side edge, wherein an outer one of the plurality of longitudinal rows of tip apertures adjacent the second longitudinal side edge is positioned closer to the second longitudinal side edge than an outer one of the plurality of longitudinal rows of tip apertures adjacent the first longitudinal side edge is positioned relative to the first longitudinal side edge, wherein a respective outer one of the plurality of shaft apertures in each of the plurality of longitudinal rows of shaft apertures adjacent the first lateral outer edge is positioned closer to the first lateral outer edge than a respective outer one of the plurality of shaft apertures adjacent the second lateral outer edge is positioned relative to the second lateral outer edge, and wherein a respective outer one of the plurality of tip apertures in each of the plurality of longitudinal rows of tip apertures adjacent the second lateral outer edge is positioned closer to the second lateral outer edge than a respective outer one of the plurality of tip apertures adjacent the first lateral outer edge is positioned relative to the first lateral outer edge.

2. The stackable pipette tip tray of claim 1, wherein the spacing between one or more of the shaft apertures within each of the plurality of longitudinal rows is discontinuous.

3. The stackable pipette tip tray of claim 1 further comprising:

a plurality of sleeves positioned adjacent to and aligned with respective ones of the plurality of shaft apertures.

4. A stack of at least first and second pipette tip trays, each of the first and second pipette tip trays comprising:

a deck having first and second opposing longitudinal side edges each having a longitudinal dimension and first and second opposing lateral outer edges each having a lateral dimension, with the longitudinal dimension being greater than the lateral dimension;

a plurality of shaft apertures configured to support a plurality of pipette tips, each of the plurality of shaft apertures having a first size or shape configured to receive a shaft of one of the plurality of pipette tips, and the plurality of shaft apertures being arranged into a plurality of longitudinal rows on the deck between the first and second longitudinal side edges; and a plurality of tip apertures, each of the plurality of tip apertures having a second size or shape that is different from the first size or shape and configured to receive a distal tip end of one of a plurality of pipette tips, and the plurality of tip apertures being arranged into a plurality of longitudinal rows on the deck with at least one of the plurality of longitudinal rows of tip apertures being located between an adjacent pair of longitudinal rows of shaft apertures, wherein the stack is configured such that the first pipette tip tray is positioned above, and is rotated relative to, the second pipette tip tray such that the first longitudinal side edge of the first pipette tip tray vertically aligns with the second longitudinal side edge of the second pipette tip tray, the second longitudinal side edge of the first pipette tip tray vertically aligns with the first longitudinal side edge of the second pipette tip tray, the first lateral outer edge of the first pipette tip tray vertically aligns with the second lateral outer edge of the second pipette tip tray, the second lateral outer edge of the first pipette tip tray vertically aligns with first lateral outer edge of the second pipette tip tray, and the plurality of shaft apertures of the first pipette tip tray vertically aligns with the plurality of tip apertures of the second pipette tip tray.

5. The stack of claim 4, wherein the first and second longitudinal side edges of the first pipette tip tray lie in respective common vertical planes with the second and first longitudinal side edges of the second pipette tip tray.

6. A pipette storage system comprising a rack and the stack of pipette tip trays of claim 4.

7. A stack of at least first and second pipette tip trays, each of the first and second pipette tip trays comprising:

a deck having first and second opposing longitudinal side edges each having a longitudinal dimension and first and second opposing lateral outer edges each having a lateral dimension, with the longitudinal dimension being greater than the lateral dimension;

a plurality of shaft apertures configured to support a plurality of pipette tips, each of the plurality of shaft apertures having a first size or shape configured to receive a shaft of one of the plurality of pipette tips, and the plurality of shaft apertures being arranged into a plurality of longitudinal rows on the deck between the first and second side edges; and a plurality of tip apertures, each of the plurality of tip apertures having a second size or shape that is different from the first size or shape and configured to receive a distal tip end of one of a plurality of pipette tips, and the plurality of tip apertures being arranged into a plurality of longitudinal rows on the deck with at least one of the plurality of longitudinal rows of tip apertures being located between an adjacent pair of longitudinal rows of shaft apertures, wherein an outer one of the plurality of longitudinal rows of shaft apertures adjacent the first longitudinal side edge is positioned closer to the first longitudinal side edge than an outer one of the plurality of longitudinal rows of shaft apertures adjacent the second longitudinal side edge is positioned relative to the second longitudinal side edge, the stack being configured such that the first pipette tip tray is positioned above, and is rotated relative to, the second pipette tip tray such that the first longitudinal side edge of the first pipette tip tray vertically aligns with the second longitudinal side edge of the second pipette tip tray, and the second longitudinal side edge of the first pipette tip tray vertically aligns with the first longitudinal side edge of the second pipette tip tray, the first lateral outer edge of the first pipette tip tray vertically aligns with the second lateral outer edge of the second pipette tip tray, the second lateral outer edge of the first pipette tip tray vertically aligns with first lateral outer edge of the second pipette tip tray, and the plurality of shaft apertures of the first pipette tip tray vertically aligns with the plurality of tip apertures of the second pipette tip tray.

8. The stack of pipette tip trays of claim 7, wherein the first and second longitudinal side edges of the first pipette tip tray lie in respective common vertical planes with the second and first longitudinal side edges of the second pipette tip tray.

9. A pipette storage system comprising a rack and the stack of pipette tip trays of claim 7.

10. A method of stacking at least first and second pipette tip trays, each of the first and second pipette tip trays having a deck with first and second opposing longitudinal side edges each having a longitudinal dimension, first and second opposing lateral outer edges each having a lateral dimension, with the longitudinal dimension being greater than the lateral dimension, a plurality of shaft apertures each having a first size or shape configured to receive shafts of a plurality of pipette tips, and a plurality of tip apertures each having a second size or shape that is different from the first size or shape and configured to receive distal tip ends of a plurality of pipette tips, the method comprising:

positioning the first pipette tip tray above the second pipette tip tray;

rotating the first pipette tip tray relative to the second pipette tip tray so that the first longitudinal side edge of the first pipette tip tray vertically aligns with the second longitudinal side edge of the second pipette tip tray, the second longitudinal side edge of the first pipette tip tray vertically aligns with the first longitudinal side edge of the second pipette tip tray, the first lateral outer edge of the first pipette tip tray vertically aligns with the second lateral outer edge of the second pipette tip tray and the second lateral outer edge of the first pipette tip tray vertically aligns with the first lateral outer edge of the second pipette tip tray; and advancing the first pipette tip tray toward the second pipette tip tray such that the distal tip ends of the plurality of pipette tips residing in the plurality of shaft apertures of the first pipette tip tray are received by the plurality of tip apertures of the second pipette tip tray.

11. The method of claim 10, wherein the plurality of shaft apertures of the first and second pipette tip trays are arranged into a plurality of longitudinal rows between the first and second longitudinal side edges and the plurality of tip apertures are arranged into a plurality of longitudinal rows with at least one of the plurality of longitudinal rows of tip apertures being located between an adjacent pair of longitudinal rows of shaft apertures.

12. The method of claim 10, wherein the first and second longitudinal side edges of the first pipette tip tray lie in respective common vertical planes with the second and first longitudinal side edges of the second pipette tip tray.

* * * * *